US00PP08601P

United States Patent [19]

Kientzler

[11] Patent Number: Plant 8,601

[45] Date of Patent: Feb. 15, 1994

[54] IMPATIENS PLANT NAMED TAHITI

[75] Inventor: Ludwig Kientzler, Gensingen, Fed. Rep. of Germany

[73] Assignee: Paul Ecke Ranch, Inc., Encinitas, Calif.

[21] Appl. No.: 872,422

[22] Filed: Apr. 23, 1992

[51] Int. Cl.[5] ..... A01H 5/00

[52] U.S. Cl. ..... Plt./87.6

[58] Field of Search ..... Plt. 87.6

*Primary Examiner*—James R. Feyrer

[57] ABSTRACT

A new and distinct cultivar of Impatiens plant named Tahiti, characterized by its large, bright pink flowers with red-purple eye, compact growth habit with excellent self-branching without pinching, medium green glossy foliage with red midveins, very early and uniform flowering, floriferous habit, and by its suitability to pot or hanging basket culture.

1 Drawing Sheet

The present invention relates to a new and distinct cultivar of plant known as Impatiens and commercially known as New Guinea Impatiens. The new cultivar is known by the cultivar name Tahiti, and was developed by the inventor Ludwig Kientzler in Gensingen, Federal Republic of Germany by crossing the cultivar designated E-390 (seed parent) with the cultivar designated E-510 (pollen parent).

Asexual reproduction by terminal (stem tip) cuttings taken by me or under my supervision at Gensingen, Federal Republic of Germany, has shown that the unique features of this new impatiens are stabilized and are reproduced true to type in successive propagations.

The following characteristics distinguish the new impatiens from both its parent varieties and other cultivars of this general type known and used in the floriculture industry:

1. Compact growth habit with good self-branching. Plants in 16.5 cm pots were 16.5 cm tall and 28 cm wide, eight weeks after planting.
2. Large, bright pink flowers with a red eye. Open flowers measure up to 6 cm in diameter.
3. Early flowering and floriferous. Plants in 16.5 cm pots were in flower 7 weeks after planting.
4. Medium green, glossy foliage.
5. Well suited both to 4" pot and 8" hanging basket culture Tahiti can be compared in certain respects to the cultivar Fiji, disclosed in a pending application of applicant. The flower color of Tahiti somewhat is similar to Fiji but Tahiti is a darker pink. A further difference is that the growth habit of Tahiti is not as compact as Fiji.

The accompanying colored photograph is a top perspective view of the new cultivar, showing color as true as it is reasonably possible to obtain in a colored reproduction of this type.

The following is a detailed description of my new impatiens cultivar based on plants grown under commercial practice in Encinitas, Calif. Plants were started as rooted cuttings and were transplanted in mid-December into 16.5 cm (6.5 inch) pots, one pot per plant. By mid-February, plants were growing vigorously and were in flower. The values, measurements and observations noted below were taken from plants in full bloom in mid-February.

Color references are made to The Royal Horticultural Society Colour Chart (R.H.S.), except where general terms of ordinary dictionary significance are used.

Parentage: Cross between E-390 (seed) and E-510 (pollen).

Asexual reproduction:

A. *Cutting type.*—Tip, with stems 2–3 cm long developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance. Pinching is not recommended since it does not enhance branching and only delays flowering by removing flower buds.

B. *Habit of growth.*—Vigorous, self-branching habit, producing whorls of leaves and flowers. Growth is indeterminate and flowering is continuous.

C. *Foliage description.*—Leaves are simple. Lower leaves on stems are opposite. Higher leaves in whorls of 3–5, but predominately 5. 1. Leaf shape: Ovate. Leaf blade tips are acuminate; bases are acute to attenuate. 2. Leaf blade size: Mature leaves typically 11 cm long and 5 to 4.5 cm wide. 3. Petiole length: 3–4 cm. 4. Leaf margin: Finely ciliated. 5. Leaf texture: Slightly rugose. a. Upper surface: Glabrous. b. Under surface: Glabrous. 6. Leaf color: Glossy and medium green with reddish midveins. a. Upper surface: Near 147A, mid-veins and stems have anthocyanin coloration, approximately 183C. b. Under surface: Greyed green, between 191A and 191B. 7. Venation: Pinnate.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus 2 rudimentary sepals fused into the under surface of the superior petal. A spur originates from the base of the inferior sepal. Spur is reddish and 5 to 5.5 cm long.

D. *Flowers borne.*—Singly, on reddish pedicels about 6 cm long.

E. *Quantity of flowers.*—One flower per leaf. Flowers occur progressively around the whorl of leaves so that tight buds to mature flowers are visible at the same time.

F. *Petals.*—Petals open nearly perpendicular to the pedicel so the plane of the flower surface is nearly flat. 1. Number of petals lateral, superior and inferior: Five (5) petals, all overlapping. 2. Shape: All petals are heart-shaped. Superior petal has a broad base. Other petals have a pointed base. 3. Color: Overall color closest to pink 62C with a small red-purple eye. a. Upper surface: Base or background color nearest to 62D, with overlying darker pink blush which is at times as dark as 62A (particularly petal margins) or as light as 62C; base of petals (eye) near 61B; petal color on a typical flower fades nonuniformly, with lateral petals being closest to 62B and superior and inferior petals fading to nearer 62C-D. Petals margin show little fading, frequently remain near 62A. b. Under surface: Near 65B. 4. Flower size: Up to 6 cm in diameter.

G. *Reproductive organs.*—Flowers are monoecious. 1. Stamens: Five (5), broad and fused to form a tube around the ovary; tinged pink. 2. Anther: Hooded and cream colored. 3. Pollen: Cream colored. 4. Stigma: Five pointed star, colorless. 5. Styles: Very short. 6. Ovary: 5-celled, 4–5 mm long until fertilized. Grows to 1 cm or longer after fertilization; green.

Resistance to disease: Good resistance to common stem and root disease, Rizoctonia and Pythium. Botrysis may be a problem in humid or mist propagation environments, but no greater than with other New Guinea Impatiens cultivars.

I claim:

1. A new and distinct cultivar of Impatiens plant named Tahiti, as illustrated and described.

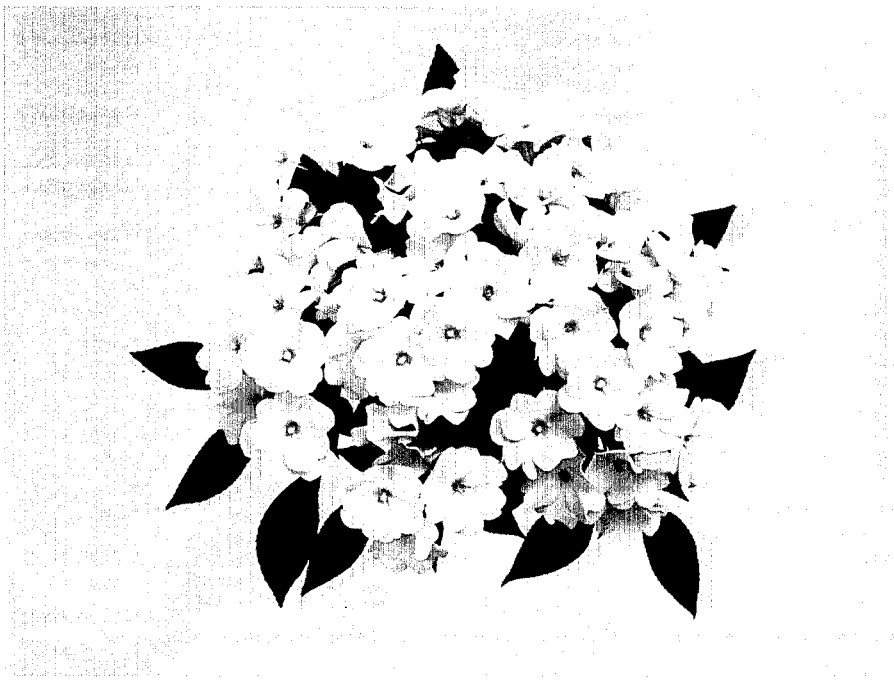

* * * * *